United States Patent [19]

Binnig et al.

[11] 4,183,935

[45] Jan. 15, 1980

[54] BISPIDINE DERIVATIVES, THEIR PREPARATION, AND DRUGS CONTAINING SAME

[75] Inventors: Fritz Binnig, Fussgoenheim; Ludwig Friedrich, Mannheim; Hans P. Hofmann, Ludwigshafen; Horst Kreiskott, Wachenheim; Claus Müeller, Viernheim; Manfred Raschack, Weisenheim, all of Fed. Rep. of Germany

[73] Assignee: BASF Aktiengesellschaft, Fed. Rep. of Germany

[21] Appl. No.: 915,119

[22] Filed: Jun. 13, 1978

[30] Foreign Application Priority Data

Jun. 13, 1977 [DE] Fed. Rep. of Germany ....... 2726571

[51] Int. Cl.² .................. A61K 31/445; C07D 471/08
[52] U.S. Cl. .................................... 424/256; 546/122; 546/123
[58] Field of Search ................... 260/293.55; 424/256; 546/122, 123

[56] References Cited

U.S. PATENT DOCUMENTS 3,962,449   6/1976   Binnig et al. .................... 260/293.55

OTHER PUBLICATIONS

Ruenitz, et al., J. of Med. Chem., 20, (1977), pp. 1668–1671.

Primary Examiner—Joseph Paul Brust
Attorney, Agent, or Firm—Keil & Witherspoon

[57] ABSTRACT

Bispidine derivatives of the formula

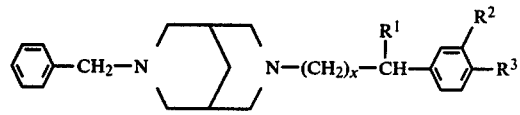

where $R^1$ is H or $C_6H_5$, $R^2$ is H, Cl or $CF_3$, $R^3$ is H, F or Cl and X is 0 or 1, and drugs which contain these compounds. The compounds are prepared by condensing N-monobenzylbispidine with appropriately substituted phenylethyl halides or by a Mannich reaction of N-benzylpiperid-4-one with appropriately substituted phenylalkylamines, followed by reduction. They exhibit mainly anti-arrhythmic action.

15 Claims, No Drawings

BISPIDINE DERIVATIVES, THEIR PREPARATION, AND DRUGS CONTAINING SAME

U.S. Pat. No. 3,962,449 discloses that certain bispidine derivatives are good anti-arrhythmic agents. We have found novel bispidine derivatives which possess an even better action than the compounds of the prior art.

The present invention relates to new bispidine derivatives of the general formula I

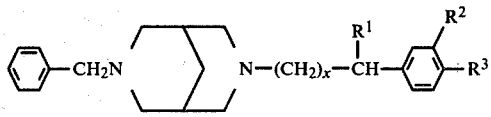

where $R^1$ is hydrogen or phenyl, $R^2$ is hydrogen, chlorine or trifluoromethyl, $R^3$ is hydrogen, fluorine or chlorine and x is 0 or 1, and to their salts with physiologically acceptable acids.

The invention further relates to a process for the preparation of compounds of the general formula I and of their salts with physiologically acceptable acids, wherein (a) N-monobenzylbispidine is reacted with a compound of the general formula II

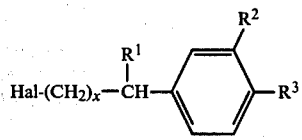

where $R^1$, $R^2$, $R^3$ and x have the above meanings, and Hal is halogen, or (b) N-benzylpiperid-4-one is subjected to a Mannich reaction with formaldehyde and an amine of the general formula III

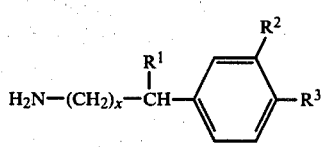

where $R^1$, $R^2$, $R^3$ and x have the same meanings as above, and the keto group in the resulting bispidone derivative is reduced,
and the compounds thus obtained are then, if required, converted to salts with physiologically acceptable acids.

Finally, the invention also relates to drugs which contain compounds of the general formula I or their salts with physiologically acceptable acids.

Examples of suitable physiologically acceptable acids are hydrochloric acid, sulfuric acid, phosphoric acid, acetic acid, malonic acid, succinic acid, fumaric acid, maleic acid, citric acid, tartaric acid, lactic acid and diaminosulfonic acid.

The reaction of N-monobenzylbispidine with the compound II may be carried out, for example, with sodium hydride in dimethylformamide, with sodium hydroxide in water or ethanol, with sodium carbonate in butanol or amyl alcohol, with potassium carbonate in water, methanol, isopropanol, butanol, amyl alcohol, acetone, acetonitrile, toluene, dimethylformamide, dimethylsulfoxide or tetrahydrofuran, with sodium methylate in methanol, with sodium isopropylate in isopropanol, with potassium tert.-butylate in tert.-butanol, tetrahydrofuran or dimethylsulfoxide, or with sodium amide in toluene or xylene. The reaction succeeds best with sodium hydride in dimethylformamide. As a rule, it is carried out at room temperature.

The Mannich reaction can be carried out in the conventional manner. Examples of suitable solvents are tetrahydrofuran, chloroform and methylene chloride, and particularly good solvents are methanol, ethanol and isopropanol. Preferred acids for use in the reaction are glacial acetic acid and hydrochloric acid. The formaldehyde can also be employed in the reaction in the form of paraformaldehyde. Advantageously, the reaction is carried out at an elevated temperature, for example at the boiling point of the solvent employed. The reduction of the keto compounds obtained is best carried out by the Kishner-Wolff method.

The new compounds and their salts have a good anti-arrhythmic action and a low toxicity.

To determine their anti-arrhythmic activity, the substances were administered orally to rats (Sprague Dawley, weight 200–250 g) 45 minutes before starting a thiobutabarbital narcosis (100 mg/kg administered intraperitoneally). Aconitine was used to produce arrhythmias, and was infused intravenously 60 minutes after administration of the active substance (dosage rate 0.005 mg/kg per minute). In the untreated animals, arrhythmias manifest themselves after an average of 3.32 minutes, and their occurrence can be delayed by anti-arrhythmic agents, the delay being dependent on the dose. The $ED_{50\%}$ is the does which increases by 50% the duration of infusion up to the occurrence of arrhythmias. R.E. is the relative effect, based on quinidine=1.00. The maximum effect is that achieved by administering the maximum tolerated dose. $\Delta\%$ indicates the percentage by which the duration of the aconitine infusion can be increased. R.M.E. is the relative maximum effectiveness, based on quinidine=1.00. The dose producing a toxic effect indicates the amount (in mg/kg) at which the first toxic symptoms such as cyanosis or changes in ECG occur. Q is the quotient of the toxic dose and the $ED_{50\%}$.

In addition to the anti-arrhythmic effect, the novel compounds and their salts possess calcium-antagonistic, antiphlogistic and thrombocyte aggregation-inhibiting properties. They are resorbed well and should be administered orally or parenterally. The daily dose is about 1–20 mg/kg for oral administration and about 0.05–1.0 mg/kg for intravenous or intramuscular administration. They may be administered in the form of, for example, tablets, dragees and solutions.

TABLE

| Compound | | | | Effective dose | | Maximum effect | | | Toxic effect | |
|---|---|---|---|---|---|---|---|---|---|---|
| $R^1$ | $R^2$ | $R^3$ | x | $ED_{50\%}$ | R.E. | Dose | $\Delta\%$ | R.M.E. | Dose | Q |
| H | Cl | H | 0 | 16.6 | 2.57 | 46.4 | 123 | 0.92 | 100 | 6.0 |
| $C_6H_5$ | H | H | 0 | 20.4 | 2.09 | 215 | 205 | 1.54 | 464 | 22.8 |

TABLE-continued

| Compound | | | | Effective dose | | Maximum effect | | | Toxic effect | |
|---|---|---|---|---|---|---|---|---|---|---|
| $R^1$ | $R^2$ | $R^3$ | x | $ED_{50\%}$ | R.E. | Dose | Δ% | R.M.E. | Dose | Q |
| H | H | F | 0 | 20.2 | 2.11 | 100 | 240 | 1.80 | 215 | 10.6 |
| H | $CF_3$ | H | 0 | 25.4 | 1.68 | 100 | 242 | 1.82 | 215 | 2.5 |
| H | Cl | Cl | 0 | 15.6 | 2.74 | 215 | 283 | 2.13 | 464 | 29.7 |
| $C_6H_5$ | H | H | 1 | 13.0 | 3.28 | 46.4 | 203 | 1.53 | 100 | 7.7 |
| Quinidine | | | | 42.7 | 1.00 | 215 | 133 | 1.00 | 464 | 10.9 |

EXAMPLE 1

(a) Preparation of the starting material 153.2 g (0.5 mole) of N,N'-dibenzylbispidine (cf. U.S. Pat. No. 3,962,449) were dissolved in 500 ml of ethanol and were hydrogenated, after adding 5 g of 5% strength palladium on charcoal, in a 2 liter flask, whilst stirring. After the absorption of hydrogen had ended, the catalyst was filtered off, the filtrate was evaporated and the residue was distilled. 93.2 g (86.3%) of N-monobenzyl-bispidine, boiling at 98°–103° C./0.06 mm Hg, were obtained.

(b) Preparation of the end product 2.4 g (0.055 mole) of a 55% strength sodium hydride suspension were added to a solution of 10.8 g (0.05 mole) of monobenzylbispidine in 100 ml of dimethylformamide. After stirring for five hours at room temperature, 8.1 g (0.05 mole) of 3-chlorobenzyl chloride were added dropwise and the mixture was stirred for a further three hours. The excess sodium hydride was decomposed with methanol. After distilling off the solvent under reduced pressure, the residue was taken up in water and extracted with ether. After drying over sodium sulfate, the ether was evaporated off. The residue was dissolved in a hot mixture of isopropanol and ethyl acetate and 6 g of fumaric acid were added. On cooling the solution, 18.4 g (=81.7%) of N-benzyl-N'-(3-chlorobenzyl)-bispidine fumarate, melting at 181°–183° C., crystallized out.

The same result was obtained on using 3-chlorobenzyl bromide instead of 3-chlorobenzyl chloride.

The following components were prepared similarly:

N-Benzyl-N'-(4-chlorobenzyl)-bispidine fumarate, melting point 137°–139° C., yield 82.4%.

N-Benzyl-N'-(4-fluorobenzyl)-bispidine fumarate, melting point 170° C., yield 86.8%.

N-Benzyl-N'-(3-trifluoromethylbenzyl)-bispidine fumarate, melting point 110° C., yield 75.5%.

N-Benzyl-N'-(3,4-dichlorobenzyl)-bispidine fumarate, melting point 104° C., yield 72.1%.

N-Benzyl-N'-benzhydryl-bispidine fumarate, melting point 195° C., yield 86.7%.

EXAMPLE 2

165 ml of glacial acetic acid were mixed with 165 ml of methanol; 65 g (0.33 mole) of 2,2-diphenylethylamine, 62.4 g (0.33 mole) of N-benzylpiperid-4-one and 24.6 g (0.82 mole) of paraformaldehyde were added successively, whilst stirring and cooling in ice, and the mixture was then refluxed for 3 hours, whilst stirring. After it had cooled, the glacial acetic acid and the methanol was substantially stripped off under reduced pressure at 50° C., the residue was taken up in 1,000 ml of methylene chloride and 20% strength sodium hydroxide solution was added, whilst stirring and cooling in ice, until a strongly alkaline reaction is obtained. The organic phase was separated off and the aqueous phase was extracted with 200 ml of methylene chloride. The combined organic phases were dried over sodium sulfate and evaporated. 135 g of crude N-benzyl-N'-2,2-diphenylethyl-bispidone were obtained. This material was dissolved in 500 ml of triethylene glycol. After adding 55 g of 85% strength potassium hydroxide, 36.6 g of 80% strength hydrazine hydrate were introduced dropwise at 60°–80° C., whilst stirring. The mixture was then heated slowly to 200°–210° C. and was kept for 3 hours at this temperature, whilst distilling off water through a 20 cm Vigreux column. After cooling, the reaction mixture was diluted with 2 liters of water and was extracted with 5 times 200 ml of diethyl ether. The combined extracts were dried over sodium sulfate and evaporated. The residue was distilled under reduced pressure, and 32.2 g of a viscous yellow oil boiling at 225°–250° C./0.12 mm Hg were obtained as the main fraction. 10 g of fumaric acid were dissolved in a small amount of isopropanol and mixed with the distillate obtained. On slow cooling, N-benzyl-N'-2,2-diphenylethylbispidine fumarate x $H_2O$ crystallized out; it was filtered off, washed with a small amount of cold isopropanol and recrystallized from isopropanol/water.

Yield: 17.2 g (=9.6%), melting point 142°–143° C.

We claim:

1. N-benzyl-N'-(3,4-dichlorobenzyl)-bispidine.
2. N-benzyl-N'-(3-chlorobenzyl)-bispidine.
3. N-benzyl-N'-(4-fluorobenzyl)-bispidine.
4. N-benzyl-N'-(3-trifluoromethylbenzyl)-bispidine.
5. N-benzyl-N'-benzhydryl-bispidine.
6. N-benzyl-N'-(2,2-diphenylethyl)-bispidine.
7. A therapeutic composition comprising an effective amount of at least one compound according to general formula I

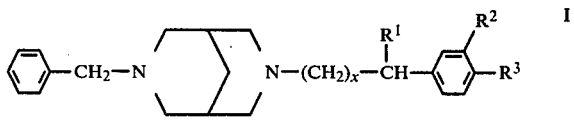

where $R^1$ is hydrogen or phenyl, $R^2$ is hydrogen, chlorine or trifluoromethyl, $R^3$ is hydrogen, fluorine or chlorine and x is 0 or 1, and its salts with a physiologically acceptable acid, with the proviso that $R^1$, $R^2$ and $R^3$ cannot all be H where x is 0 in association with a therapeutically acceptable carrier.

8. A therapeutic composition comprising an effective amount of the compound claimed in claim 1 in association with a therapeutically acceptable carrier.

9. A therapeutic composition comprising an effective amount of the compound claimed in claim 2 in association with a therapeutically acceptable carrier.

10. A therapeutic composition comprising an effective amount of the compound claimed in claim 3 in association with a therapeutically acceptable carrier.

11. A therapeutic composition comprising an effective amount of the compound claimed in claim 4 in association with a therapeutically acceptable carrier.

12. A therapeutic composition comprising an effective amount of the compound claimed in claim 5 in association with a therapeutically acceptable carrier.

13. A therapeutic composition comprising an effective amount of the compound claimed in claim 6 in association with a therapeutically acceptable carrier.

14. A composition for the oral treatment of cardiac arrhythmias which contains from 30 to 60 mg of at least one compound as described in claim 7, in association with a therapeutically acceptable carrier.

15. A composition for the parenteral treatment of cardiac arrhythmias, which contains from 10 to 30 mg of a compound as described in claim 7 in association with a therapeutically acceptable carrier.

* * * * *